United States Patent
Esposito et al.

(10) Patent No.: US 9,464,975 B2
(45) Date of Patent: Oct. 11, 2016

(54) COMPOSITE TEST SPECIMEN

(71) Applicant: The Boeing Company, Chicago, IL (US)

(72) Inventors: Jack J. Esposito, Auburn, WA (US); Joshua S. Dustin, Mason, OH (US)

(73) Assignee: The Boeing Company, Chicago, IL (US)

( * ) Notice: Subject to any disclaimer, the term of this patent is extended or adjusted under 35 U.S.C. 154(b) by 153 days.

(21) Appl. No.: 14/458,961

(22) Filed: Aug. 13, 2014

(65) Prior Publication Data
US 2016/0047723 A1 Feb. 18, 2016

(51) Int. Cl.
*G01N 3/08* (2006.01)
*G01N 33/00* (2006.01)

(52) U.S. Cl.
CPC .......... *G01N 3/08* (2013.01); *G01N 2033/0003* (2013.01); *G01N 2203/0019* (2013.01); *G01N 2203/0096* (2013.01); *G01N 2203/0298* (2013.01)

(58) Field of Classification Search
CPC .......... G01N 3/08; G01N 2203/0019; G01N 2203/0096; G01N 2203/0298; G01N 2033/0003; G01N 3/04; G01N 3/24; G01N 2203/0025; G01N 2203/0252; G01N 2203/0423; G01N 2203/0435; G01N 29/043; G01N 33/44; G01N 2291/2694; G01N 29/30; G01N 2291/0231; G01N 2203/0664; Y10T 156/1056; Y10T 156/1089; Y10T 428/249953
USPC ......... 73/818, 831, 866, 856, 799, 819–823, 73/841, 842, 845
See application file for complete search history.

(56) References Cited

U.S. PATENT DOCUMENTS

| | | | |
|---|---|---|---|
| 5,280,730 A | 1/1994 | Peres et al. | |
| 5,284,063 A * | 2/1994 | Newell | G01N 3/08 73/822 |
| 5,528,942 A * | 6/1996 | Baratta | G01N 3/02 73/818 |
| 6,655,218 B1 * | 12/2003 | Ogisu | B29C 70/088 73/768 |
| 2005/0109124 A1 * | 5/2005 | Greszczuk | G01N 3/04 73/862 |
| 2013/0084434 A1 * | 4/2013 | Kehrl | B29C 70/207 428/174 |

FOREIGN PATENT DOCUMENTS

EP  1 750 123 A2  2/2007

OTHER PUBLICATIONS

Designation: D695—10; Standard Test Method for Compressive Properties of Rigid Plastics; ASTM International; Jul. 1, 2014; (7 pgs).
Adams; Thickness-tapered unidirectional composite specimens: CompositesWorld; retrieved from Internet—http://www.printfriendly.com/print/?source=site&url=http://www.compositesworld.com—Jul. 3, 2014; (3 pgs).
U.S. Appl. No. 13/769,485, filed Feb. 18, 2013, 20 pages.
Extended European Search Report for European Application No./ Patent No. 15178111.9-1553; dated Dec. 18, 2015; (7 pages).

* cited by examiner

*Primary Examiner* — Lisa Caputo
*Assistant Examiner* — Brandi Hopkins
(74) *Attorney, Agent, or Firm* — Toler Law Group, PC (57) ABSTRACT

A particular composite test specimen includes a first tab, a second tab, and a gage section between the first tab and the second tab. The first tab, the second tab, and the gage section are machined from a composite test blank. The composite test blank includes a plurality of plies arranged with first ply layers having fibers oriented in a first direction and second ply layers having fibers oriented in a second direction, where the first direction is different than the second direction.

19 Claims, 6 Drawing Sheets

602 — Use a plurality of plies (e.g., arrange pre-impregnated (pre-preg) plies) to form a composite layup by arranging first ply layers to have fibers oriented in a first direction and arranging second ply layers to have fibers oriented in a second direction, the first direction different than the second direction, the first direction different than the second direction, wherein the composite layup has a first face and a second face opposite the first face 604 — Cut the composite layup to form a first section and a second section, the first section having a third face corresponding to the first face of the composite layup and a fourth face corresponding to the second face of the composite layup, and the second section having a fifth face corresponding to the first face of the composite layup and a sixth face corresponding to the second face of the composite layup 606 — Couple the third face of the first section to the fifth face of the second section and curing to form a composite panel 608 — Form one or more composite test blanks from the composite panel (e.g., by milling or cutting the composite panel)

610 — Machine a particular composite test blank of the one or more composite test blanks to form a composite test specimen, the composite test specimen having a first tab, a second tab, and a gage section between the first tab and the second tab (e.g., mill sides of the particular composite test blank to be substantially parallel to the first direction and form the gage section by reducing a thickness of the particular composite test blank by removing material from both faces of the particular composite test blank)

612 — Couple a first cap plate to an end of the first tab, the first cap plate covering the end of the first tab and covering at least a portion of one or more sides and/or at least a portion of one or more faces of the first tab 614 — Couple a second cap plate to an end of the second tab, the second cap plate covering the end of the second tab and covering at least a portion of one or more sides and/or at least a portion of one or more faces of the second tab 616 — Adhere a strain gage to the gage section of the composite test specimen

FIG. 6

COMPOSITE TEST SPECIMEN

FIELD OF THE DISCLOSURE

The present disclosure is generally related to composite test specimens.

BACKGROUND

To reliably predict a failure response of composite materials, ply level progressive failure analysis using material properties of the composite material may be used. Material properties of composite materials may be determined using standardized methodologies. For example, the ASTM D695-10 standard describes a methodology for testing the compressive property of rigid plastics. However, ply level progressive failure analysis tends to be sensitive to fiber direction material properties, and current standardized methodologies are not able to provide sufficiently reliable fiber direction material property information. For example, current test methodologies for measurement of fiber direction strength and strain tend to produce spurious failure modes leading to underestimation of critical compressive material properties.

Some causes of the spurious failure modes may be related to the manner in which composite test specimens are prepared. Composite test specimens used for compressive testing are typically prepared by bonding end tabs onto a sample of a material to be tested. The bonded end tabs can introduce problems, which may lead to premature failure of the composite test specimen. For example, the bonded ends tabs may lead to brooming of fibers. As a result, even with use of standard test methods, actual compressive failure limits of fibers of a composite test specimen may be underestimated. Additionally, spacing constraints (e.g., an amount of distance between the end tabs), may prevent performing direct strain measurements on the composite test specimen during testing. Accordingly, valuable information that could be gained by direct strain measurement is not available.

SUMMARY

In a particular embodiment, a composite test specimen includes a first tab, a second tab, and a gage section between the first tab and the second tab. The first tab, the second tab, and the gage section are machined from a composite test blank. The composite test blank includes a plurality of plies arranged with first ply layers having fibers oriented in a first direction and second ply layers having fibers oriented in a second direction, where the first direction is different than the second direction.

In another particular embodiment, a method includes using a plurality of plies to form a composite assembly by arranging first ply layers to have fibers oriented in a first direction and arranging second ply layers to have fibers oriented in a second direction, where the first direction is different than the second direction. The composite assembly has a first face and a second face opposite the first face. The method includes cutting the composite assembly to form a first section and a second section. The first section has a third face corresponding to the first face of the composite assembly and a fourth face corresponding to the second face of the composite assembly, and the second section has a fifth face corresponding to the first face of the composite assembly and a sixth face corresponding to the second face of the composite assembly. The method also includes coupling the third face of the first section to the fifth face of the second section to form a composite panel and forming one or more composite test blanks from the composite panel.

In another particular embodiment, a composite test blank includes a first stack of plies and a second stack of plies. The first stack of plies and the second stack of plies are sections of a single composite assembly. The single composite assembly includes first ply layers having fibers oriented in a first direction and second ply layers having fibers oriented in a second direction. The single composite assembly has a first face and a second face opposite the first face. The first stack of plies has a third face corresponding to the first face of the single composite assembly and a fourth face corresponding to the second face of the single composite assembly. The second stack of plies has a fifth face corresponding to the first face of the single composite assembly and a sixth face corresponding to the second face of the single composite assembly. The third face of the first stack of plies is coupled to the fifth face of the second stack of plies.

The features, functions, and advantages described can be achieved independently in various embodiments or may be combined in other embodiments, further details of which are disclosed with reference to the following description and drawings.

DETAILED DESCRIPTION

By forming a test specimen from a composite material (e.g., a composite test specimen) using methods described herein, compressive properties of the composite material may be measured more accurately (e.g., by avoiding early failure of the test specimen). In a particular embodiment, a test specimen is prepared from (e.g., milled from) a single composite blank rather than by bonding end tabs to a sample of a material to be tested. To illustrate, a composite panel (formed using methods described herein) is cut or otherwise machined to provide one or more composite test blanks. A composite test blank may be machined (e.g., milled, ground, cut, etc.) to remove material (e.g., portions of ply layers) to form a gage section between tabs. Thus, the gage section and tabs are each integral to and formed from a single composite assembly. The composite test specimen may include additional features that reduce premature failure mechanisms, such as premature buckling between the gage section and the tabs and brooming of ends of the tabs. Further, a cross-ply layup may be used to form the composite assembly to reduce or restrict premature transverse tension failures of 0-degree plies.

FIGS. 1A-1D are diagrams illustrating a particular embodiment of a method of forming a composite assembly 140. The composite assembly 140 may be cured to form a composite panel (such as the composite panel 200 of FIG. 2), which may be used to form one or more composite test blanks. The composite assembly 140 may be formed by arranging a plurality of plies (e.g., plies 121-128) to form a composite layup 102. The plies 121-128 may be arranged in a cross-ply layup. In the cross-ply layup, first ply layers (e.g., plies 121, 122, 124, 125, 126, and 127) have fibers arranged in a first direction, and second ply layers (e.g., plies 123 and 128) have fibers oriented in a second direction, where the second direction is different than the first direction. For example, an angle between the second direction and the first direction may be approximately 90-degrees. In the example provided in FIGS. 1A-1D, the first ply layers (e.g., plies 121, 122, 124, 125, 126, and 127) have fibers oriented in a 0-degree direction, and the second ply layers (e.g., plies 123 and 128) have fibers oriented in a 90-degree direction (as indicated by a fiber orientation key in FIG. 1D).

The cross-ply arrangement of the composite layup 102 enables placement of 0-degree plies (plies with fibers oriented in the 0-degree direction) away from areas of high stress concentration (such as at reentrant corners, as described with reference to FIGS. 4 and 5) by surrounding the 0-degree plies with 90 degree plies (plies with fibers oriented in the 90-degree direction). The cross-ply arrangement of the composite layup 102 also results in use of a relatively small number (e.g., 2 to 3) of 0-degree plies in a gage section of a composite test specimen (as illustrated in FIG. 5) to reduce a load required to cause compressive failure. This reduction in load reduces the risk of inducing a premature end failure during compressive testing. The specific arrangement of plies be changed somewhat from one composite layup 102 to another arrangement of plies (not shown) based on the cured ply thickness of the material used. For example, more ply layers or fewer ply layers may be used. As another example, a different proportion or arrangement of 0-degree plies to 90-degree plies may be used.

Figure 1A:
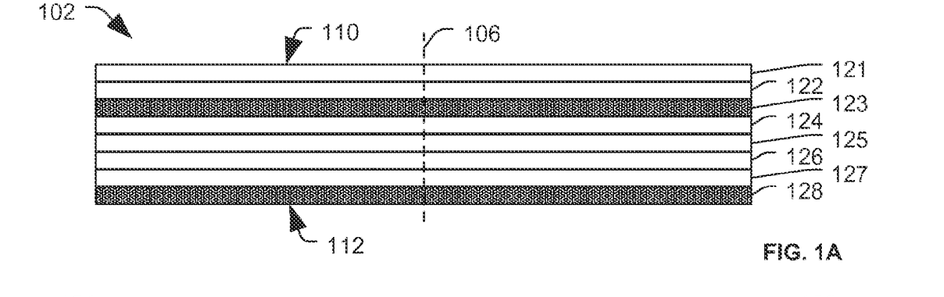
FIGS. 1A, 1B, 1C and 1D are diagrams illustrating a particular embodiment of a method of forming a composite assembly.

The composite layup 102 may be formed using a plurality of pre-impregnated ("pre-preg") plies that are stacked or otherwise arranged as illustrated in FIG. 1A. After debulking and possibly performing some machining steps (such as cutting down, squaring or otherwise treating edges, corners or faces of the composite layup 102), and before curing, the composite layup 102 may be divided into sections, e.g., along section line 106.

Figure 1B:
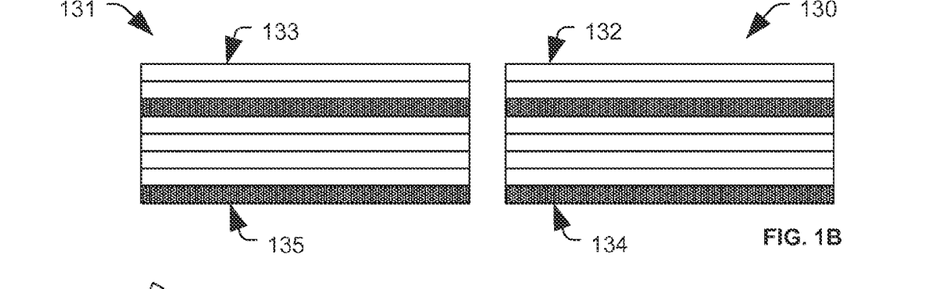

Referring to FIG. 1B, a first section 131 and a second section 130 of the composite layup 102, divided along the section line 106, are shown. The first section 131 has a third face 133 corresponding to a first face 110 of the composite layup 102. Additionally, the first section 131 has a fourth face 135 corresponding to a second face 112 of the composite layup 102. Likewise, the second section 130 has a fifth face 132 corresponding to the first face 110 of the composite layup 102 and has a sixth face 134 corresponding to the second face 112 of the composite layup 102. It is noted that the figures are not to scale. Accordingly, although the sections 130 and 131 are illustrated in FIG. 1B as having approximately the same size and shape, the sections 130 and 131 may have the same size and shape or different sizes and/or shapes, depending on particular design constraints or preferences.

Figure 1C:
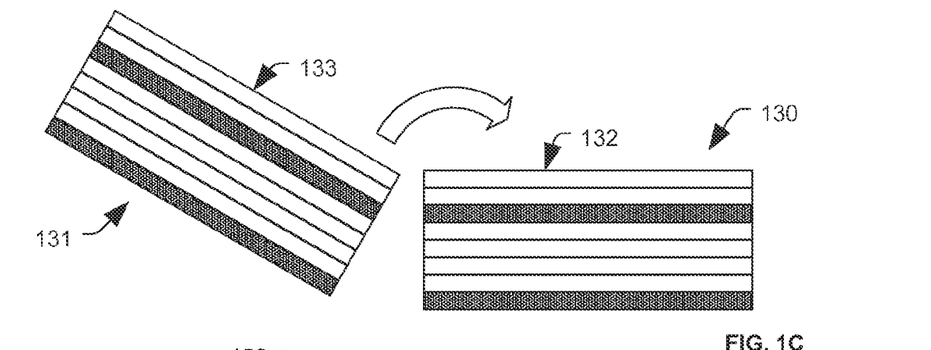

Referring to FIG. 1C, the first section 131 may be flipped over and coupled to the second section 130. For example, the third face 133 of the first section 131 may be coupled to the fifth face 132 of the second section 130 to form a composite assembly 140 (shown in FIG. 1D). Thus, the composite assembly 140 includes multiple stacks of plies including a first stack of plies corresponding to the first section 131 and a second stack of plies corresponding to the second section 130, where both the first stack of plies and the second stack of plies are formed from a single composite layup (e.g., the composite layup 102 of FIG. 1A). Although the first stack of plies corresponding to the first section 131 and the second stack of plies corresponding to the second section 130 are illustrated, in other embodiments more than two stacks of plies may be formed from a single composite layup.

Figure 1D:
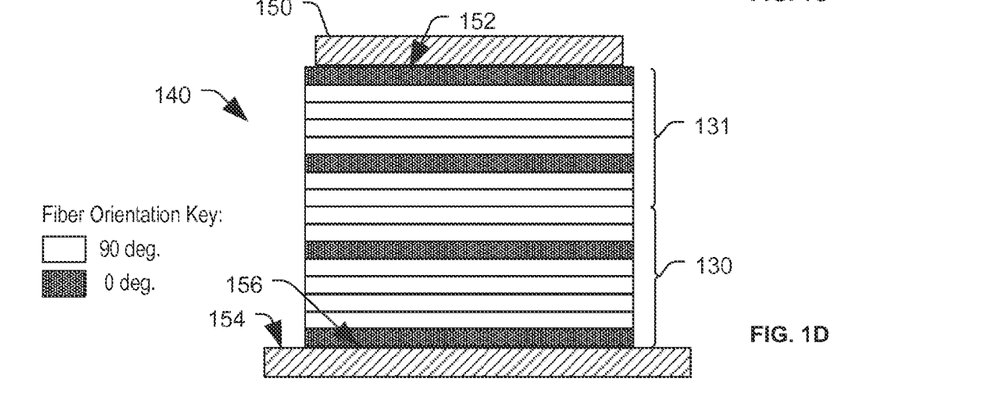
Figure 2:
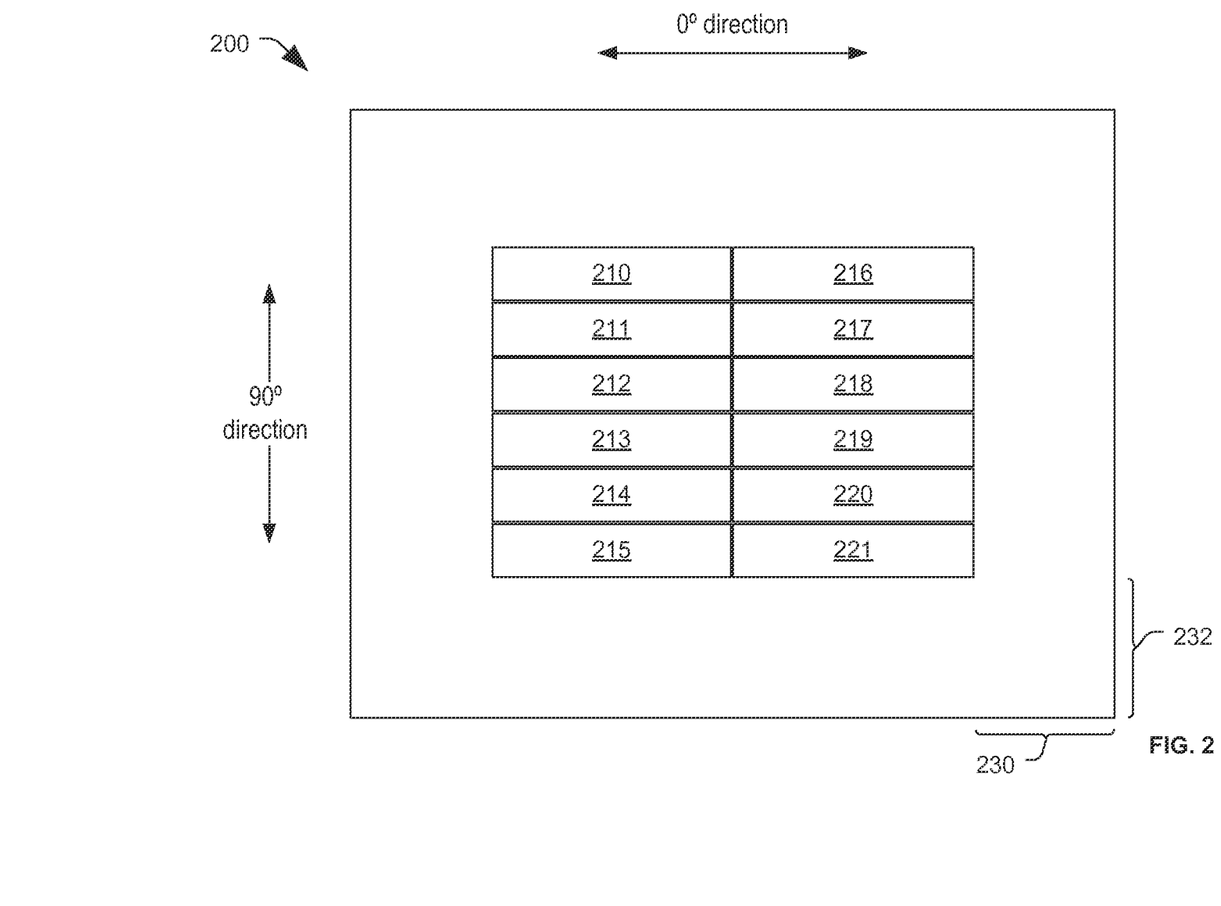
FIG. 2 is a diagram of a top view of a particular embodiment of the composite panel formed from the composite assembly of FIG. 1.

Referring to FIG. 1D, after the composite assembly 140 is formed, the composite assembly 140 may be cured to form a composite panel (such as the composite panel 200 of FIG. 2). Curing may be performed with the composite assembly 140 placed on a relatively flat surface 154. Additionally, a caul plate 150 may be applied to the composite assembly 140 during curing. The caul plate 150 and the flat surface 154 enable the composite layup 102 to cure with a relatively smooth first face 152 and a relatively smooth second face 156.

FIG. 2 is a diagram of a top view of a particular embodiment of a composite panel 200 formed by curing the composite assembly 140 of FIG. 1D. The composite panel 200 may be divided (e.g., cut or milled) into a plurality of composite test blanks, such as composite test blanks 210-221. For example, edges 230 and 232 of the composite panel 200 may be cut away (or otherwise removed), and a central portion of the composite panels 200 may be used to form the composite test blanks 210-221. Each composite test blank 210-221 may have a length oriented along the 0-degree direction described with reference to FIG. 1A-1D and a width oriented along the 90-degree direction. Although the composite panel 200 is divided into twelve composite test blanks in FIG. 2, in other embodiments the composite panel 200 may be divided into more than twelve composite test blanks or fewer than twelve composite test blanks.

Figure 3:
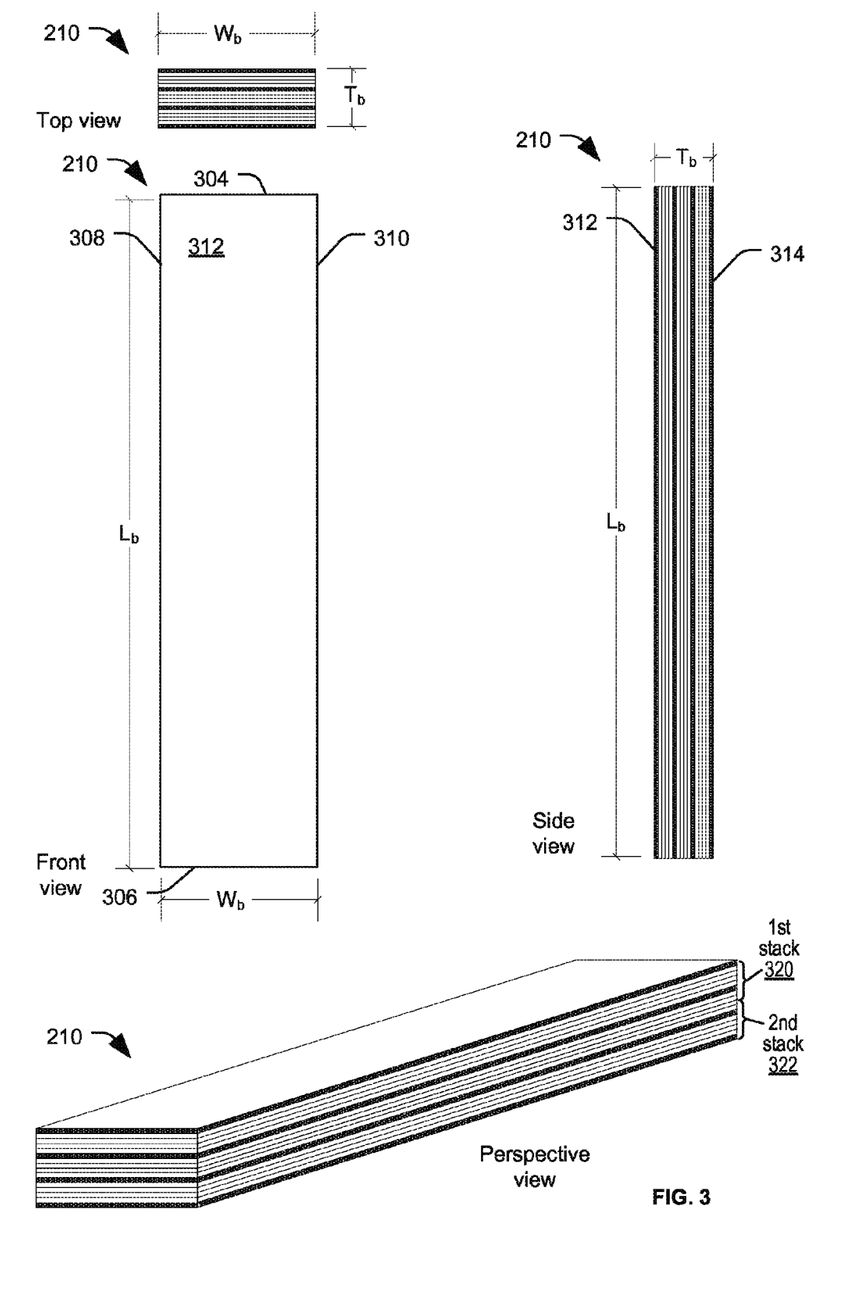
FIG. 3 is a diagram of multiple views of a particular embodiment of a composite test blank formed from the composite panel of FIG. 2.

FIG. 3 is a diagram of multiple views of a particular embodiment of a composite test blank formed from the composite panel 200 of FIG. 2. FIG. 3 shows a particular composite test blank 210 in more detail via a top-view, a front-view, a side-view, and a perspective-view. The composite test blank 210 has a first end 304 and a second end 306. Between the first end 304 and the second end 306, the composite test blank 210 has a length $L_b$. The composite test blank 210 also has a first side 308 and a second side 310. Between the first side 308 and second side 310, the composite test blank 210 has a width $W_b$. The composite test blank 210 also has a first face 312 and a second face 314. Between the first face 312 and second face 314, the composite test blank 210 has a thickness $T_b$.

The composite test blank 210 may be formed of a plurality of ply layers as described with reference to FIGS. 1A-1D. The plurality of ply layers may include two or more stacks of plies, such as a first stack of plies 320 and a second stack of plies 322. The first stack of plies 320 and the second stack of plies 322 may be formed during a single composite layup. For example, as described with reference to FIG. 1A-1D, the single composite layup (e.g., the composite layup 102) may be formed to have a first face (e.g., the first face 110 of FIG. 1A) and a second face (e.g., the second face 112 of FIG. 1A) opposite the first face. Before curing, the single composite layup may be divided into sections such that a first section (e.g., the first section 131 of FIG. 1B) has a third face (e.g., the third face 133 of FIG. 1B) and a fourth face (e.g., the fourth face 135 of FIG. 1B), and a second section (e.g., the second section 130 of FIG. 1B) has a fifth face (e.g., the fifth face 132 of FIG. 1B) and a sixth face (e.g., the sixth face 134 of FIG. 1B). The first section may correspond to the first stack of plies 320 and the second section may correspond to the second stack of plies 322. For example, the third face of the first section may be coupled to the fifth face of the second section to form a composite assembly (such as the composite assembly 140 of FIG. 1D). The composite assembly may be cured to form a composite panel, which may be cut into composite test blanks (as described with reference to FIG. 2).

The composite test blank 210 may be used to form a composite test specimen. For example, the composite test blank 210 may be machined (e.g., cut, milled, ground, or otherwise acted upon using a subtractive manufacturing process) to form the composite test blank.

Figure 4:
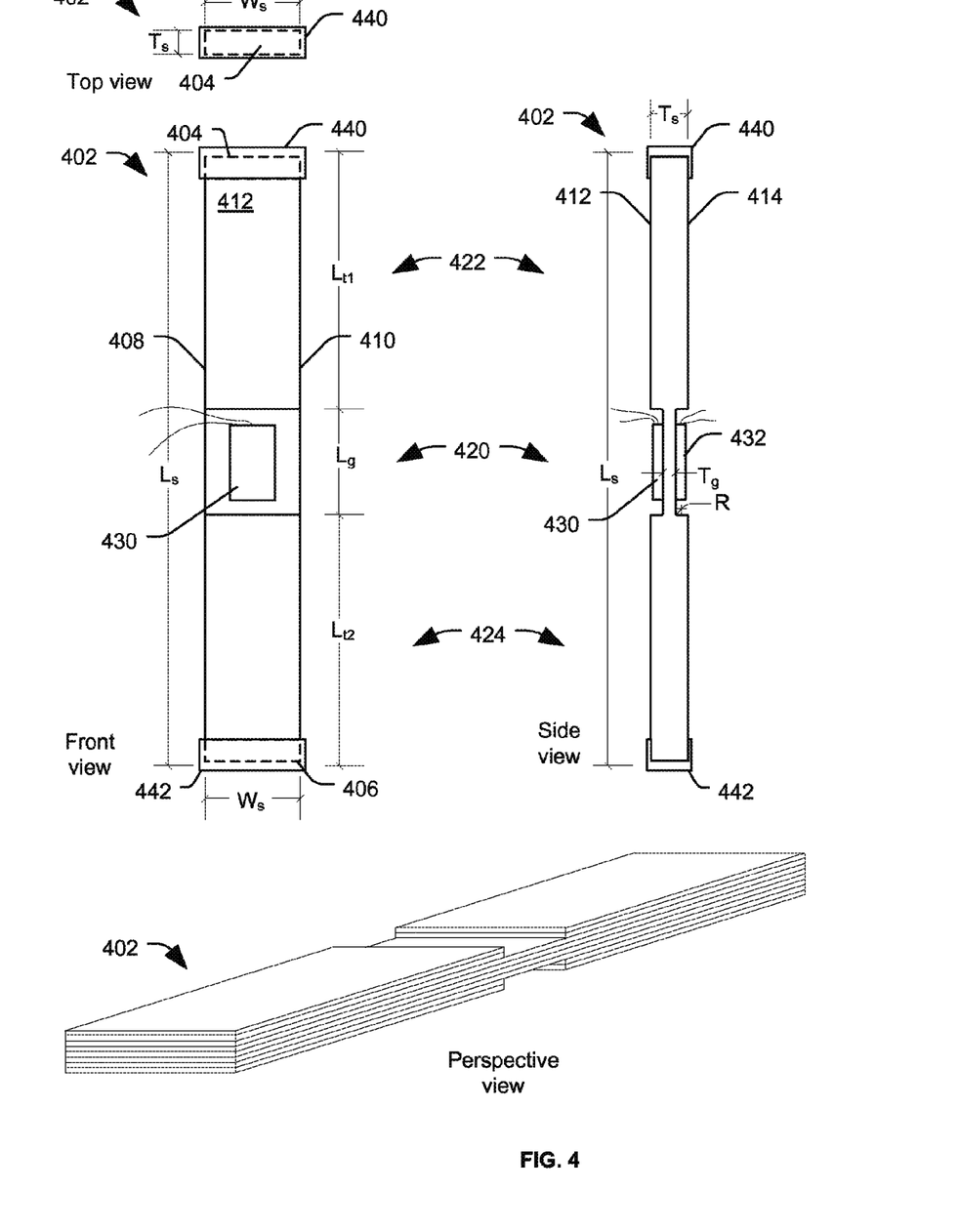
FIG. 4 is a diagram of multiple views of a particular embodiment of a composite test specimen formed from the composite test blank of FIG. 3.
Figure 5:
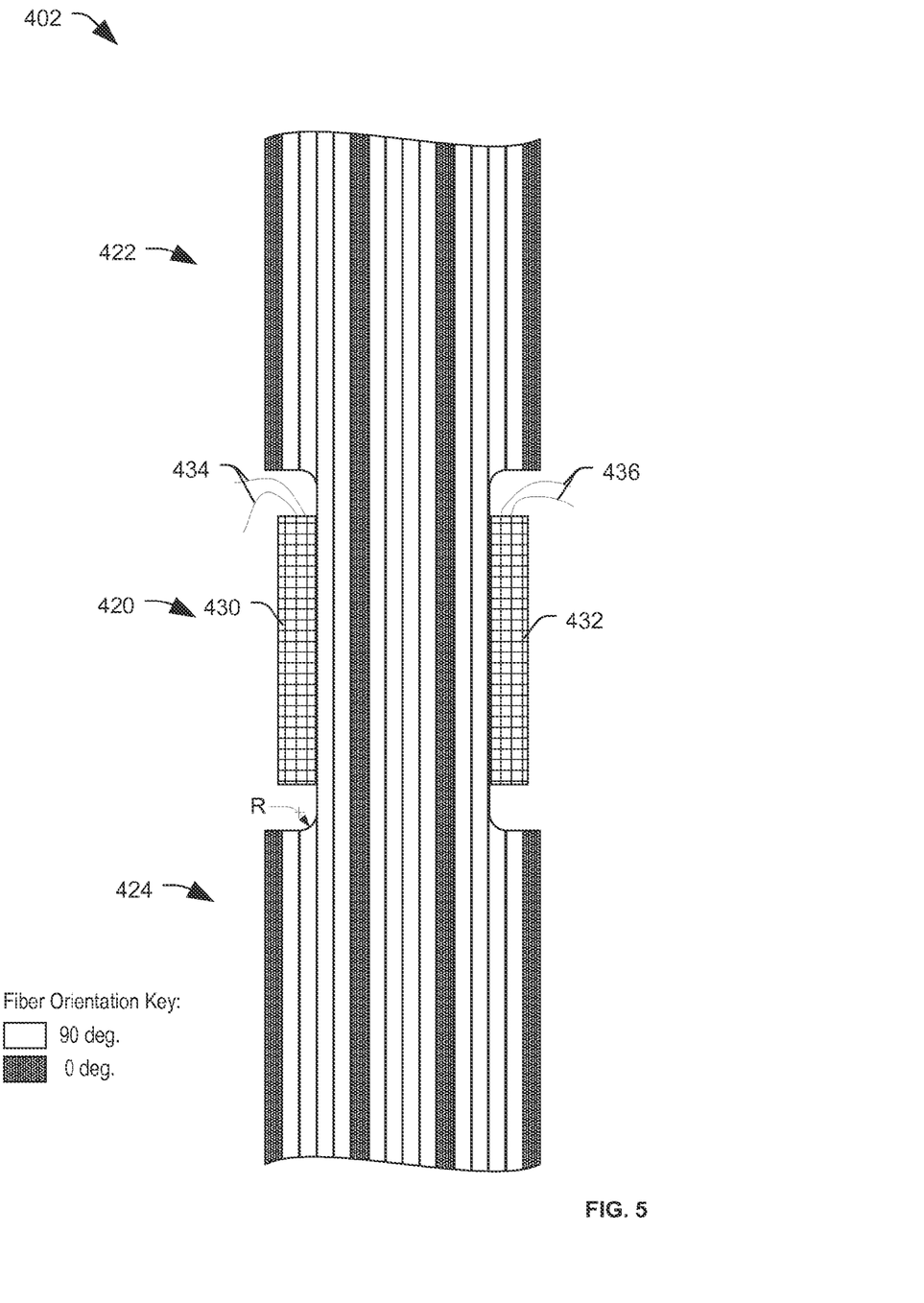
FIG. 5 is a diagram of detailed side view of a particular embodiment of the composite test specimen of FIG. 4.

FIGS. 4 and 5 are diagrams of various views of a particular embodiment of a composite test specimen 402 formed from the composite test blank 210 of FIG. 3. In FIG. 4, the composite test specimen 402 has a first end 404 and a second end 406. Between the first end 404 and second end 406, the composite test specimen has a length Ls. Additionally, the composite test specimen 402 has a first side 408 and a second side 410. Between the first side 408 and second side 410, the composite test specimen 402 has a width Ws. Further, the composite test specimen 402 has a first face 412 and a second face 414. Between the first face 412 and second face 414, the composite test specimen 402 has a thickness of Ts. In a particular embodiment, the length $L_s$, the width $W_s$, and the thickness $T_s$ may be selected to enable use of the composite test specimen 402 with a testing apparatus (e.g., a testing apparatus as described in the ASTM D695-10 standard). For example, the length $L_s$ may be about 3.10 inches (within a tolerance of ±0.03 inches), the width $W_s$ may be about 0.500 inches (within a tolerance of ±0.005 inches), and the thickness $T_s$ may be about 0.135 inches. The thickness $T_s$ may vary from one composite test specimen to another as a result of how the composite assembly cures in various areas, as well as for other reasons (such as differences in materials being tested).

To form the composite test specimen 402 from the composite test blank 210 the length, the width, the thickness, or a combination thereof, of the composite test blank 210 may be reduced. For example, the width $W_s$ of the composite test specimen 402 may be less than the width $W_b$ of the composite test blank 210. To illustrate, the composite test blank 210 may be machined (e.g., milled, cut, ground or otherwise acted upon using a subtractive manufacturing process) to reduce the width $W_b$ to the width $W_s$. The machining may also shape other dimensions of the composite test specimen 402, such as squaring the sides 408, 410 relative to the ends 404, 406 and/or relative to the faces 412, 414. Further, the machining may shape the composite test specimen 402 such that the sides 408, 410 are each substantially parallel to fibers oriented in the 0-degree direction.

The composite test blank 210 may also, or in the alternative, be machined (e.g., milled, cut, ground or otherwise acted upon using a subtractive manufacturing process) to reduce the length $L_b$ to the length $L_s$. The machining may also shape other dimensions of the composite test specimen 402, such as squaring the ends 404, 406 relative to the sides 408, 410 and/or relative to the faces 412, 414.

The composite test specimen 402 may include a first tab 422 and a second tab 424. Between the first tab 422 and the second tab 424, the composite test specimen 402 may include a gage section 420. The first tab 422 and second tab 424 may be integral with (as opposed to adhered to) the gage section 420. The gage section 420 has a thickness Tg corresponding to a first number of ply layers, the first tab 422 includes a second number of ply layers, and the second tab 424 includes a third number of ply layers. The first number of ply layers (corresponding to the gage section 420) is less than the second number of ply layers and is less than the third number of ply layers. The gage section 420 may be formed by reducing a thickness of the composite test blank 210 from both faces 412 and 414 of the composite test blank 210 (e.g., by reducing a number of plies of the gage section 420 relative to a number of plies of the composite test blank 210). To illustrate, as shown in the side-view and perspective-view of FIG. 4, the gage section 420 may correspond to a portion of the composite test specimen 402 where the thickness $T_s$ is reduced to the thickness $T_g$, which is less than the thickness $T_s$. In a particular embodiment, the thickness $T_g$ is about 0.075 inches. Approximately half of the material that is removed to reduce the thickness of the gage section 420 from the thickness $T_s$ to the thickness $T_g$ is removed from each face. To illustrate, if the thickness $T_s$ is about 0.135 inches and the thickness $T_g$ is about 0.075 inches, about 0.060 inches of material needs to be removed to go from $T_s$ to $T_g$. Approximately half of the 0.060 inches of material (i.e., about 0.030 inches of material) is removed from the first face 412, and approximately half of the 0.060 inches of material (i.e., about 0.030 inches of material) is removed from the second face 414. Thus, the gage section 420 may be formed by machining (e.g., cutting, milling, grinding, etc.) the composite test blank 210 in a direction that is perpendicular to the stacks of plies (e.g., a direction normal to the first face 312, the second face 314, or both) to reduce the number of plies in the stack in the gage section 420 and to reduce the thickness of the gage section to a predetermined amount.

As illustrated in FIG. 4, the tabs 422, 424 and the gage section 420 are formed as integral portions of the original composite panel. Accordingly, the tabs 422, 424 and the gage section 420 are similarly affected by environmental condition (e.g., temperature, humidity, etc.). Thus, the composite test specimen 402 may be less prone to disbond during extreme environment testing than traditional test coupons (e.g., test coupons that use bonded end-tabs on a sample of test material). Additionally while bonding tabs to a test material to form a traditional test coupon uses a special bonding fixture, no such fixture is used to form tabs 422 and 424, which reduces time and resources that would be used to manufacture the traditional test coupons. The tabs 422, 424 also help to maintain very high tolerances in the coupon geometry because they can be precisely machined while forming the composite test specimen (e.g., without worrying about debonding a bonded end tab from a sample of test material).

In a particular embodiment, the gage section 420 is formed by machining (e.g., milling, cutting, grinding or otherwise acting upon using a subtractive manufacturing process) the faces 412 and 414 of the composite test blank 210. The machining process may also form a curved reentrant corner between the gage section 420 and each of the tabs 422 and 424. For example, each reentrant corner of the gage section 420 may have a radius of curvature R as illustrated in FIG. 4. In a particular embodiment, the radius of curvature R of each reentrant corner is about 0.020 inches (within a tolerance of ±0.005 inches). The curvature of the reentrant corners may reduce stress concentration at the corners, thereby reducing risk of early failures at the interface between the gage section 420 and each tab 422, 424 during testing.

A length $L_g$ of the gage section 420 may be sized such that a strain gage can be directly adhered to the gage section 420. For example, the length $L_g$ may be about 0.30 inches in order to accommodate a 0.25 inch strain gage. In FIG. 4, a first strain gage 430 is coupled to (e.g., adhered to) the gage section 420 at a first face of the gage section 420, and a second strain gage 432 is coupled to the gage section 420 at a second face of the gage section 420. Thus, the strain gages 430, 432 enable direct measurement of strain during compressive testing, providing more detailed information than can be gathered using conventional test specimens.

The composite test specimen 402 may also include a first cap plate 440 coupled to the first end 404 of the first tab 422 and a second cap plate 442 coupled to the second end 406 of the second tab 424. The first cap plate 440 may cover the first end 404 of the first tab 422 and may cover at least a portion of one or more sides 408, 410, at least a portion of one or more faces 412, 414 of the first tab 422, or a combination thereof. For example, the first cap plate 440 may include a metal piece that is formed or machined with a groove, slot or opening to fit over the first end 404 of the first tab 422. Likewise, the second cap plate 442 may cover the second end 406 of the second tab 424 and may cover at least a portion of one or more sides 408, 410, at least a portion of one or more faces 412, 414 of the second tab 424, or a combination thereof. For example, the second cap plate 442 may include a metal piece that is formed or machined with a groove, slot or opening to fit over the second end 406 of the second tab 424. The cap plates 440, 442 may inhibit brooming of ends of respective tabs 422, 424 when the ends are subject to end-loaded compression testing.

FIG. 5 is a diagram of a detailed side view of a particular embodiment of the composite test specimen 402 of FIG. 4. In particular, FIG. 5 illustrates a more detailed view of the gage section 420 and an area connecting the gage section 420 to the first tab 422 and to the second tab 424. FIG. 5 also illustrates orientations of fibers of the ply layers and provides further illustration of the radius of curvature R of the reentrant corners and attachment of the strain gages 430, 432 to the composite test specimen 402.

In FIG. 5, the strain gages 430, 432 are directly adhered to the gage section 420. Leads 434, 436 of the strain gages 430, 432 may protrude from the gage section 420 to enable measurement of strain during testing. Each reentrant corner may have the radius of curvature R to reduce strain at the reentrant corner during testing. As illustrate in FIG. 5, a majority of plies of the composite test specimen have a 90-degree fiber orientation with remaining plies having a 0-degree fiber orientation. The 0-degree fiber orientation plies reduce the risk of premature transverse tension failures.

Figure 6:
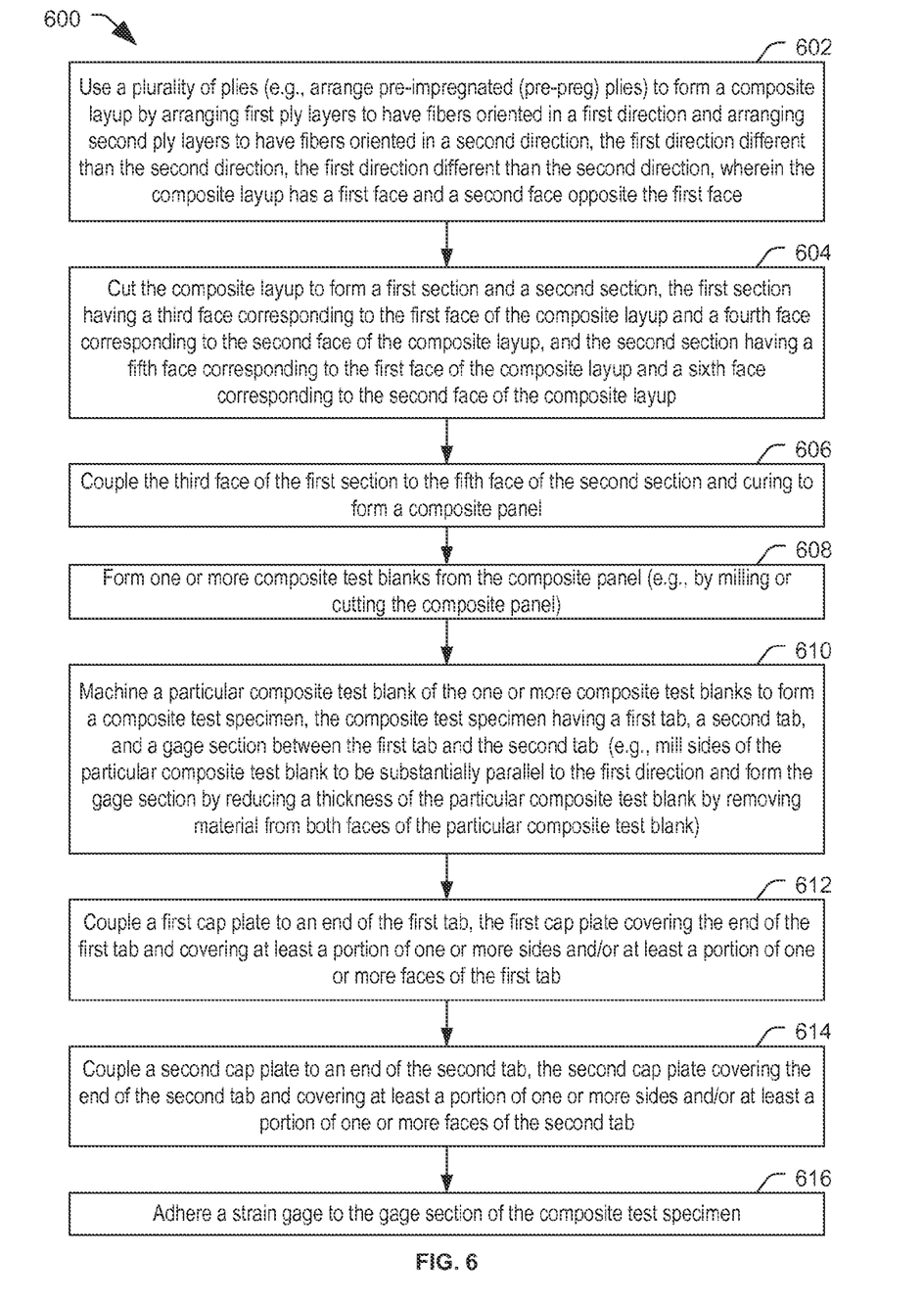
FIG. 6 is a flow chart illustrating a particular embodiment of a method of forming a composite test specimen.

FIG. 6 is a flow chart illustrating a particular embodiment of a method 600 of forming a composite test specimen. The method 600 may be used to form the composite test specimen 402 of FIGS. 4 and 5. Further, portions of the method 600 may be used to form the composite test blank 210 of FIG. 3.

The method 600 includes, at 602, using a plurality of plies to form a composite layup by arranging first ply layers to have fibers oriented in a first direction and arranging second ply layers to have fibers oriented in a second direction, where the first direction is different than the second direction. The composite layup has a first face and a second face opposite the first face. For example, the plurality of plies 121-128 of FIG. 1 may be arranged to form the composite layup 102 of FIG. 1A.

The method 600 may also include, at 604, cutting the composite assembly to form a first section and a second section. For example, the composite layup 102 of FIG. 1A may be divided into the first section 131 and the second section 130 of FIG. 1B.

As described with reference to FIG. 1B, the first section 131 has the third face 133, which corresponds to the first face 110 of the composite layup 102, and the first section 131 has the fourth face 135, which corresponds to the second face 112 of the composite layup 102. Additionally, the second section 130 has the fifth face 132, which corresponds to the first face 110 of the composite layup 102, and has the sixth face 134, which corresponds to the second face 112 of the composite layup 102. The method 600 also includes, at 606, coupling the third face of the first section to the fifth face of the second section and to form a composite assembly. The composite assembly may be cured to form a composite panel, such as the composite panel 200 of FIG. 2.

The method 600 may also include, at 608, forming one or more composite test blanks from the composite panel. For example, the composite panel 200 of FIG. 2 may be machined (e.g., cut, milled, ground, etc.) to form the composite test blanks 210-221.

The method 600 may also include, at 610, machining a particular composite test blank of the one or more composite test blanks to form a composite test specimen. For example, the composite test blank 210 of FIGS. 2 and 3 may be machined (e.g., milled, cut, ground, etc.) to form the composite test specimen 402 of FIGS. 4 and 5. To illustrate, machining the particular composite test blank to form the composite test specimen may include machining the gage section perpendicular to the first direction and perpendicular to the second direction to reduce a number of plies in the gage section relative to a number of plies of the particular composite test blank. As described with reference to FIG. 4, the composite test specimen may have a first tab, a second tab, and a gage section between the first tab and the second tab. Thus, the composite test specimen is formed from a single composite layup (e.g., corresponding to the composite layup 102 of FIG. 1A) rather than including multiple parts (e.g., a sample of a material to be tested with bonded end tabs).

The method 600 may also include, at 612, coupling a first cap plate to an end of the first tab and, at 614, coupling a second cap plate to an end of the second tab. Each cap plate may cover an end of the respective tab and cover at least a portion of one or more sides, at least a portion of one or more faces of the respective tab, or a combination thereof. For example, the first cap plate 440 of FIG. 4 covers the first end 404 of the first tab 422 and extends to cover at least a portion of a side and/or a portion of a face of the first tab 422. Likewise, the second cap plate 442 covers the second end 406 of the second tab 424 and extends to cover at least a portion of a side and/or and a portion of a face of the second tab 424.

The method 600 may also include, at 616, adhering a strain gage to the gage section of the composite test specimen. For example, the strain gages 430 and 432 may be coupled to the gage section 420, as in FIGS. 4 and 5. Leads of the strain gages 430, 432 may be routed to monitoring equipment to enable real-time monitoring of strain during compressive testing of the composite test specimen.

After the composite test specimen is formed, the composite test specimen may be used to perform testing to gather information regarding compressive properties of materials used to form the composite test specimen. For example, the ASTM D695-10 standard methodology or a modified version thereof may be used to test the composite test specimen. In the modified version, a test fixture described in the ASTM D695-10 standard may be modified to accommodate the composite test specimen. For example, an additional lower load plate may be added to the test fixture to prevent premature end failure by eliminating the space between an out-of-plane buckling guide of the test fixture and a bottom load plate of the test fixture. Addition of the lower load plate may result in the composite test specimen being supported to the end of the buckling guide. As another example, out-of-plane buckling guides of the test fixture may be flipped such that smooth surfaces of the out-of-plane buckling guides contact the composite test specimen (rather than allowing V-notched surfaces of the out-of-plane buckling guides to contact the composite test specimen as prescribed in the ASTM D695-10 standard). Flipping the out-of-plane buckling guides may reduce end buckling failure of the composite test specimen due to contact with the V-notched surfaces. As a further example, support bolts of the test fixture may be torqued to 1 in-lb, which may reduce friction between the test fixture and the composite test specimen.

Thus, after the composite test specimen is prepared (e.g., machined from a composite test blank and coupled to cap plates and strain gages), the composite test specimen may be secured in the modified test fixture and 1 in-lb of torque may be applied to the support bolts. The composite test specimen is secured to the modified test fixtures such that the composite test specimen is centered in the test fixture and such that ends of the composite test specimen squarely contact the test fixture. An end cap is placed on a top end of the composite test specimen and a load platen is moved so that it comes in contact with the end cap. The composite test specimen is loaded to failure while the load/strain response is monitored.

In a test using a composite test specimen formed of a particular composite material using the methods described herein, ultimate fiber compressive strain in excess of 21000 µ-strain at room temperature dry test conditions and 24000 µ-strain at cold temperature dry test conditions were measured. These results are in contrast to results generated for the same particular composite material using a bonded end tab test specimen, which provided measured ultimate fiber compressive strains of 7000 µ-strain at room temperature dry test conditions and 8000 µ-strain at cold temperature dry test conditions.

Embodiments described above are illustrative and do not limit the disclosure. It is to be understood that numerous modifications and variations are possible in accordance with the principles of the present disclosure.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it is to be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to fewer than all of the features of any of the disclosed embodiments.

What is claimed is:

1. A composite test specimen comprising:
a first tab including a plurality of plies arranged with first ply layers having first fibers oriented in a first direction and second ply layers having second fibers oriented in a second direction, the first direction different from the second direction;
a second tab including the first ply layers and the second ply layers; and
a gage section positioned between the first tab and the second tab, the gage section including the first ply layers and the second ply layers, wherein a number of plies in the gage section is less than a number of plies of the first tab and a number of plies of the second tab.

2. The composite test specimen of claim 1, wherein the first tab, the second tab, and the gage section are machined from a composite test blank, the composite test blank includes at least two stacks of plies formed from a single composite layup, the at least two stacks of plies including:
a first stack of plies from a first section of the single composite layup; and
a second stack of plies from a second section of the single composite layup.

3. The composite test specimen of claim 2, wherein the first stack of plies is coupled to the second stack of plies before the single composite layup was cured, and wherein the second section is adjacent the first section in the single composite layup.

4. The composite test specimen of claim 2, wherein the single composite layup has a first face and a second face opposite the first face, wherein the first stack of plies has a third face corresponding to the first face of the single composite layup and a fourth face corresponding to the second face of the single composite layup, wherein the second stack of plies has a fifth face corresponding to the first face of the single composite layup and a sixth face corresponding to the second face of the single composite layup, and wherein the third face of the first stack of plies is coupled to the fifth face of the second stack of plies to form the composite test blank.

5. The composite test specimen of claim 2, wherein the first direction is rotated approximately 90 degrees relative to the second direction, and wherein the first ply layers include a fewer number of layers than the second ply layers.

6. The composite test specimen of claim 5, wherein the first direction is along a length of the composite test blank, the length corresponding to a direction from the first tab toward the second tab, and wherein the second direction is across a width of the composite test blank.

7. The composite test specimen of claim 5, wherein sides of the first tab and the second tab are substantially parallel to the first direction, and wherein the gage section is formed by removal of material from both faces of the composite test blank to reduce a thickness of the composite test blank, and wherein a portion of the gage section proximate a center of the thickness of the composite test blank is curved.

8. The composite test specimen of claim 1, further comprising a strain gage coupled to the gage section.

9. The composite test specimen of claim 1, further comprising:
    a first cap plate coupled to an end of the first tab, the first cap plate covering the end of the first tab and covering at least a portion of one or more sides, at least a portion of one or more faces of the first tab, or a combination thereof; and
    a second cap plate coupled to an end of the second tab, the second cap plate covering the end of the second tab and covering at least a portion of one or more sides, at least a portion of one or more faces of the second tab, or a combination thereof,
    wherein the first cap plate and the second cap plate are configured to inhibit brooming of ends of respective tabs when the ends are subject to end-loaded compression testing.

10. A method comprising:
    forming a composite layup by arranging first ply layers to have first fibers oriented in a first direction and arranging second ply layers to have second fibers oriented in a second direction, the first direction different from the second direction, wherein the composite layup has a first face and a second face opposite the first face;
    cutting the composite layup to form a first section and a second section, the first section having a third face corresponding to the first face of the composite layup and a fourth face corresponding to the second face of the composite layup, and the second section having a fifth face corresponding to the first face of the composite layup and a sixth face corresponding to the second face of the composite layup;
    coupling the third face of the first section to the fifth face of the second section to form a composite panel; and
    forming one or more composite test blanks from the composite panel.

11. The method of claim 10, further comprising machining a particular composite test blank of the one or more composite test blanks to form a composite test specimen, the composite test specimen having a first tab, a second tab, and a gage section positioned between the first tab and the second tab, the gage section including the first ply layers and the second ply layers, wherein a number of plies in the gage section is less than a number of plies of the first tab and a number of plies of the second tab.

12. The method of claim 11, wherein machining the particular composite test blank to form the composite test specimen includes machining the gage section perpendicular to the first direction and perpendicular to the second direction, and wherein a number of plies in the gage section is less than a number of plies of the particular composite test blank.

13. The method of claim 11, further comprising:
    coupling a first cap plate to an end of the first tab, the first cap plate covering the end of the first tab and covering at least a portion of one or more sides, at least a portion of one or more faces of the first tab, or a combination thereof; and
    coupling a second cap plate to an end of the second tab, the second cap plate covering the end of the second tab and covering at least a portion of one or more sides, at least a portion of one or more faces of the second tab, or a combination thereof,
    wherein the first cap plate and the second cap plate inhibit brooming of ends of respective tabs when the composite test specimen is subject to end-loaded during compression testing.

14. The method of claim 11, wherein machining the particular composite test blank to form the composite test specimen includes:
    milling sides of the particular composite test blank to be substantially parallel to the first direction; and
    forming the gage section by removing material from both faces of the particular composite test blank to reduce a thickness of the particular composite test blank, wherein a portion of the gage section proximate a center of the thickness of the particular composite test blank is curved.

15. The method of claim 10, wherein the plurality of plies used to form the composite layup include pre-impregnated (pre-preg) plies, and further comprising curing the pre-preg plies while a first face of the composite layup contacts a substantially smooth surface and while a second face of the composite layup contacts a substantially smooth caul plate.

16. The method of claim 10, wherein the first section and the second section are adjacent to one another in the composite layup.

17. The method of claim 10, wherein the first direction is rotated approximately 90 degrees relative to the second direction and wherein the first ply layers include fewer layers than the second ply layers.

18. The method of claim 17, wherein the first direction is along a length of the one or more composite test blanks and wherein the second direction is across a width of the one or more composite test blanks.

19. A composite test blank comprising:
    a first stack of plies; and
    a second stack of plies, wherein the first stack of plies and the second stack of plies are sections of a single composite layup, the single composite layup including:
        first ply layers having first fibers oriented in a first direction; and
        second ply layers having second fibers oriented in a second direction, the first direction different than the second direction, and
    wherein the single composite layup has a first face and a second face opposite the first face, wherein the first stack of plies has a third face corresponding to the first face of the single composite layup and a fourth face corresponding to the second face of the single composite layup, wherein the second stack of plies has a fifth face corresponding to the first face of the single composite layup and a sixth face corresponding to the second face of the single composite layup, and wherein the third face of the first stack of plies is coupled to the fifth face of the second stack of plies.

* * * * *